United States Patent [19]
Yasukawa et al.

[11] Patent Number: 5,086,286
[45] Date of Patent: Feb. 4, 1992

[54] GAS-SENSITIVE DEVICE

[75] Inventors: Yoshikazu Yasukawa; Norihiro Inagaki, both of Hamamatsu, Japan

[73] Assignee: Kurabe Industrial Co., Ltd., Shizuoka, Japan

[21] Appl. No.: 563,321

[22] Filed: Jul. 26, 1990

[30] Foreign Application Priority Data

Jul. 28, 1989 [JP] Japan .................. 1-196131

[51] Int. Cl.$^5$ .............................. H01C 7/00
[52] U.S. Cl. ........................ 338/34; 73/23.2
[58] Field of Search ............. 338/34, 35; 422/98; 502/339, 325; 427/419.1, 419.2; 73/23.2, 23.22, 31.05, 31.06, 23.25

[56] References Cited

U.S. PATENT DOCUMENTS

| | | | |
|---|---|---|---|
| 3,950,980 | 4/1976 | Braun et al. | 338/34 X |
| 4,857,275 | 8/1989 | Furusaki et al. | 422/98 |
| 4,928,513 | 5/1990 | Sugihara et al. | 338/34 X |
| 4,938,928 | 7/1990 | Koda et al. | 422/98 |
| 4,967,589 | 11/1990 | Yagawara et al. | 73/23.25 |

FOREIGN PATENT DOCUMENTS 59-99243A 6/1984 Japan .

Primary Examiner—Marvin M. Lateef
Attorney, Agent, or Firm—Spencer & Frank

[57] ABSTRACT

A thin film gas-sensitive device includes an insulating substrate having a pair of electrodes, a gas-sensitive layer having a gas sensitive substance deposited on the insulating substrate and electrodes, and a catalytic layer deposited on the gas-sensitive layer and insulating substrate as a non-continuous layer. The insulating substrate is partly uncovered because the electrodes, the gas-sensitive layer containing the gas-sensitive substance and the catalytic layer do not thoroughly cover the substrate.

16 Claims, 5 Drawing Sheets

— 980 nm

— 246 nm

— 246 nm

GAS-SENSITIVE DEVICE

BACKGROUND OF THE INVENTION

1. Field of the Invention

The present invention relates to a gas-sensitive device with a characteristic gas-sensitive property which can prevent the reduction in the gas-sensitivity during its use and which is stable for a long period.

2. Background Information

Conventionally, various studies have been made on gas-sensitive substances such as oxide semiconductor, etc., which change their resistance in contact with various kinds of gases. In such gas-sensitive devices, catalysts are used for improving sensitivity and selectivity. For example, a certain gas-sensitive device is constructed to have a catalytic layer on its gas-sensitive substance, However, the catalyst may gradually diffuse into the gas-sensitive substance of the gas-sensitive device having this structure. Consequently, such a device may not have a stable gas-sensing property for a long period, which has induced various attempts for the improvement of the above drawbacks. One of the proposed solutions is illustrated in the Japanese Patent Application Laid-Open No. 59-99243 which employs a thin film containing $Al_2O_3$, etc. as a carrier and a metal as a catalyst.

As is described in "the Background of the Invention" and "the Problems that the Invention is to solve" sections of the Japanese Patent Application Laid-Open No. 59-99243, a catalytic layer of a thick-film type is formed through the process of application and sintering of a material in paste. Therefore, the thus obtained layer does not show good reproductivity. There is also pointed out a problem that there may be observed some deviation in the gas-sensitive property of the obtained layer. A gas-sensitive device generally equipped with a heater detects gas while heating a gas-sensitive substance. When the film is thick as in this case, a temperature gradient may be induced in the catalytic layer whereby thermal stress may be induced, causing the occurrence of a crack, etc. in the catalytic layer. The above-described drawbacks have been solved by preparing the catalytic layer into thin film. Nevertheless, the catalytic layer still needs carrier such as $Al_2O_3$, etc., so that essentially its structure must be complex. Furthermore, the device of the Japanese Patent Application Laid-Open No. 59-99243 has a sensitivity to 200 ppm CO gas of about 30, meaning that there has not yet been obtained a device with a high sensitivity.

SUMMARY OF THE INVENTION

The CO-gas detecting device according to the present invention is obtained by forming a film containing as the principal ingredient at least one of Sn or In, depositing Pt as a catalytic layer on the surface of a gas-sensitive film layer obtained by oxidizing the principal ingredient, and mixing Au with $SnO_2$ to improve the CO-gas sensitivity of the device.

The object of the present invention is to provide a device which has a simple structure without containing a carrier such as $Al_2O_3$, etc. resulting in a high gas sensitivity, and which shows a gas-sensitive property stable for a long period.

The present invention relates to a gas-sensitive device comprising a gas-sensitive substance arranged on an insulating substrate, a catalytic layer and a pair of electrodes, wherein the insulating substrate is partly not covered by the gas-sensitive substance on which is formed a catalytic layer comprising at least one of Pt and Pd, the layer being of an average thickness of 5 nm or less.

The gas-sensitive substance comprising, for example, a metallic oxide semiconductor, is formed directly by the deposition method, the sputtering method, and the like, or is formed by oxidizing the metal prepared also into film. The thin film comprising a gas-sensitive substance of an average thickness of about 20 nm or less, does not completely cover the insulating substrate. When microscopically examined, the partial absence of the gas-sensitive substance is clearly observed on the insulating substrate, although the film itself is apparently consistent. When forming a catalytic layer by the deposition method, the sputtering method, etc., utilizing the film in such condition, the catalytic layer may be formed not only on the gas-sensitive substance but also directly on the insulating substrate. The catalyst in such status is considered to hardly diffuse into the gas-sensitive substance, so that the gas-sensitive property of the device may be stabilized for a prolonged time. Such structure of the device, which has a partly exposed insulating substrate because the gas-sensitive substance may not completely cover the substrate, may be formed by known methods such as masking, etching, etc. By the term average thickness is meant the film thickness when all the atoms constituting the thin film formed on the substrate are arranged in uniform manner. When measuring a reductive gas such as CO, $H_2$, etc. as a gaseous subject for measurement, the oxide semiconductor comprising each system comprising $SnO_2$, $In_2O_3$ and ZnO in general use may be employed as the gas-sensitive substance.

According to the present invention, the sensitivity of the CO-gas detecting device employing a gas-sensitive layer containing $SnO_2$ as the principal ingredient, may be improved, by mixing 900 parts or less by weight of Au with 100 parts by weight of Sn in the gas-sensitive layer. When the mixed amount of Au exceeds 900 parts by weight per 100 parts by weight of Sn, $SnO_2$ may not keep its semiconductivity, resulting in a substantial undetectability of gas.

The catalyst to be used in the present invention may comprise for example noble metals, which are formed into such catalytic layer by the deposition method, the sputtering method, etc. For the catalyst described above, Pt and Pd may be preferable. Pt and Pd, both of an average thickness 5 nm or less are more preferable. In case of the catalyst of an average thickness exceeding 5 nm, the gas-sensitive device cannot keep its property as a semiconductor, resulting in the greatly reduced gas detecting property thereof.

For the substrate used in the present invention, there may be used heat-resistant, insulating substrates such as ceramic substrate comprising $Al_2O_3$, $SiO_2$, etc. For the electrode, Au, Pt, etc. may be used, which are formed into the electrode by the deposition method, the sputtering method, etc. The electrode may be arranged either between the gas-sensitive substance and the substrate, or between the gas-sensitive substance and the catalyst.

DETAILED DESCRIPTION OF THE PREFERRED EMBODIMENT(S)

The present invention will now be described by numbered Examples with reference to the figures.

EXAMPLE 1

Figure 1:
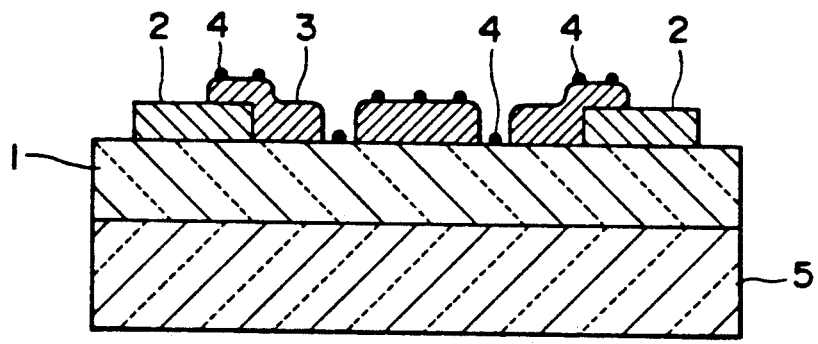
FIG. 1 is a sectional view for explaining Examples of the present invention.
Figure 2:
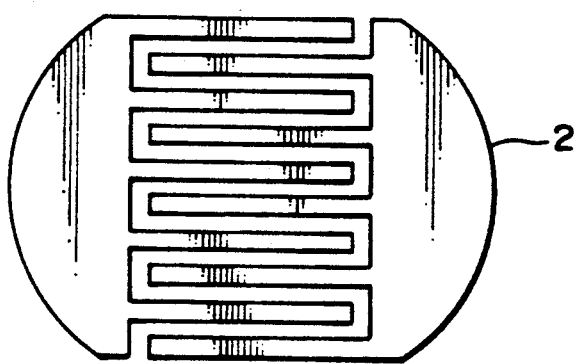
FIG. 2 is a plan view of an example of a comb-shape Au electrode.

As is shown in FIG. 1, a quartz substrate 1 of a size of approximately 15×15×0.5 mm is prepared as an insulating substrate, on which comb-shape Au electrodes 2 of a 50 nm thickness are arranged. On the substrate and the electrodes, tin used as a gas-sensitive substance 3 is deposited in vacuum. The average thickness of the thus produced film may be from about 13 to 50 nm. The film is then subjected to thermal treatment at 400° C. for 30 seconds to obtain a film comprising oxidized tin.

As is shown in FIG. 1, the $SnO_2$ layer 3 does not cover the entire surface of the substrate.

However, the average thickness represents a thickness assuming the substrate were covered uniformly. The thickness may be measured by a method using a quartz crystal oscillator. Pt 4 is deposited on the upper surface of the film 3 to form a catalytic layer 4 of about 2 nm average thickness shown as dots. Furthermore, a heating unit 5 is arranged on the back surface of the above-described insulating substrate 1.

Figure 3:
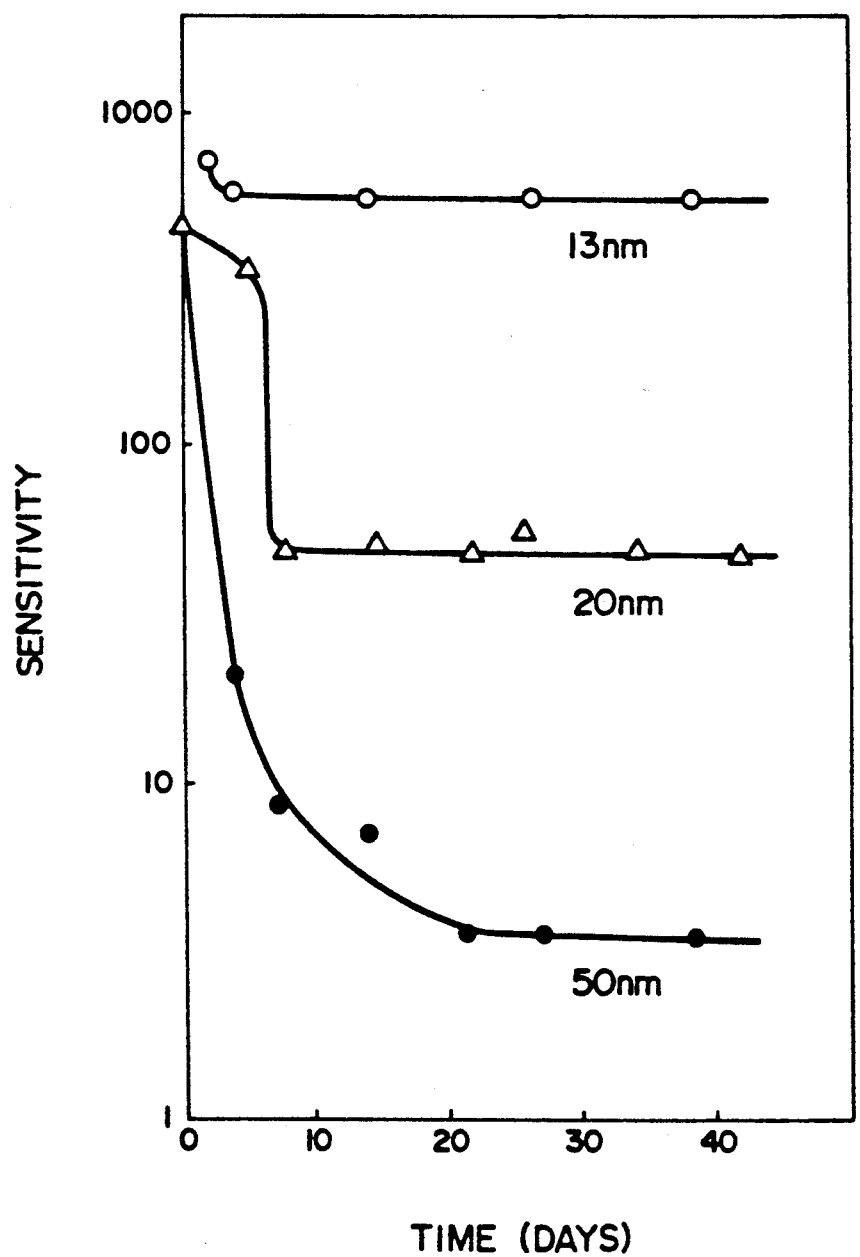
FIG. 3 is a graph showing the property of sensitivity of the gas-sensitive device over time.

According to the present Example 1, three gas-sensitive devices were constructed in the above manner, each having a tin layer with an average thickness of 50 nm, 20 nm and 13 nm, respectively. These devices were subjected to a test of their characteristics under the following conditions:

The three kinds of gas-sensitive devices were fixed in a sealed vessel and kept at 150° C. and were analyzed regarding the electrical resistance of their individual thin films in a CO atmosphere of 1000 ppm, while injecting CO gas into the vessel through an injector under stirring with a fan. The sensitivity was determined as a ratio of the electrical resistance in the CO gas atmosphere to the electrical resistance in air. FIG. 3 shows the sensitivity of the gas-sensitive devices over time. The device with a tin layer having an average thickness of about 50 nm decreased in sensitivity from about 500 to about 4 after the lapse of about 20 days. The device with a tin layer having an average thickness of about 20 mn decreased in sensitivity gradually but on the eighth day and thereafter it was stable at about 50. The device with a tin layer having an average thickness of about 13 nm shows a sensitivity of about 600, which was stable for a long time.

For comparison with the Examples presented in the Japanese Patent Application Laid-Open No. 59-99243, the electrical resistance of the devices was measured in a 200 ppm CO atmosphere. The present device with a tin layer having an average thickness of about 13 nm showed a higher sensitivity of about 500, compared with the sensitivity of about 30 proposed by the product of the Japanese Patent Application Laid-Open No. 59-99243.

Figure 4:
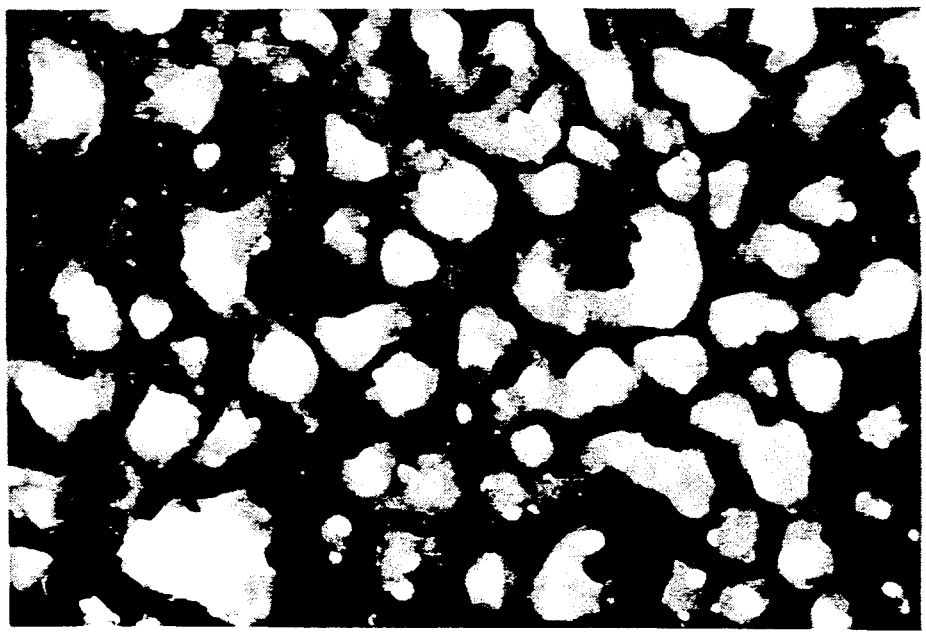
FIGS. 4 through 6 are the electron scanning miroscopic photographs reperesenting the surface of the gas-sensitive device of the present invention.
Figure 5:
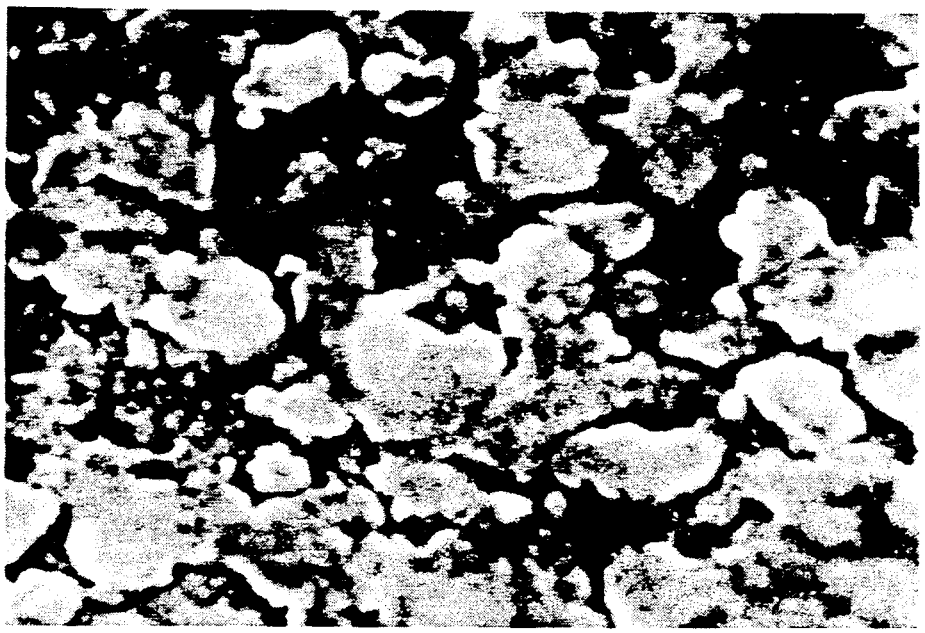
Figure 6:
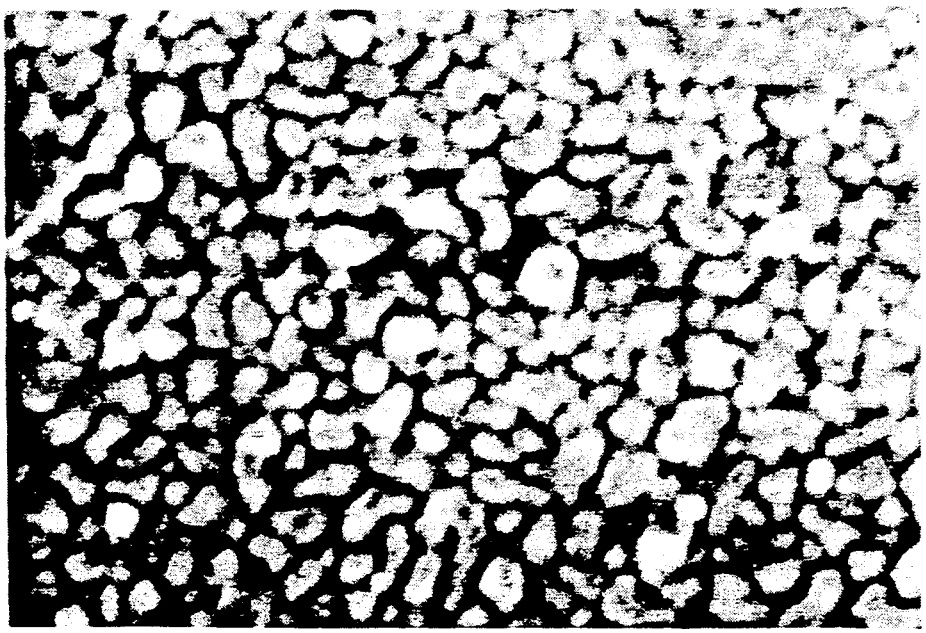

FIG. 4 is an electron scanning microscopic photograph (×10,000) representing the surface condition of the device with a tin layer having an average thickness of about 50 nm. The insulating substrate 1 is in a condition completely covered with the gas-sensitive substance 3. As Pt diffuses into the gas-sensitive substance 3, its gas sensitivity gradually reduces. As is shown in the electron scanning microscopic photograph (×40,000) of FIG. 5, the substrate 1 is partly not covered with the gas-sensitive substance 3 in the case of the device with a tin layer of an average thickness of about 20 nm. Thus, the catalyst 4 arranged directly on the insulating substrate 1 may hardly diffuse into the gas-sensitive substance 3 so its sensitivity does not decrease as greatly. As is shown in the electron scanning microscopic photograph (×40,000) of FIG. 6, a large part of the substrate 1 is not covered with the gas-sensitive substance 3 in the case of the device with a tin layer having an average thickness of about 13 nm. Thus, some of the catalyst 4 is arranged directly on the insulating substrate 1 with no contact with the gas-sensitive substance 3. In such condition, the catalyst 4 may not diffuse into the gas-sensitive substance 3, leading to the stable sensitivity of the device.

The film thickness of the catalytic layer 4 according to the present invention will now be described.

There were prepared three kinds of devices with the same structure as those used in the above Example 1, each having a catalytic layer 4 comprising Pt of an average thickness of 0.1 nm, 3 nm and 6 nm, respectively while the average thickness of the tin layer of the devices was restricted to 13 nm.

Their properties were examined under the same conditions as described above (1000 ppm CO atmosphere). There was obtained a sensitivity of about 450 in the case of the catalytic layer of 0.1 nm; about 400 in the case of that of 3 nm, while no sensitivity in the case of that of 6 nm. These results indicate that a higher sensitivity ranging between 400 and 600 may be observed in the catalytic layer 4 of an average thickness 0.1 to 3 nm, which may be the most preferable range for the average thickness. As the average thickness increases, the device cannot remain a semiconductor. The device with an average thickness exceeding 5 nm, does not have sufficient sensitivity.

EXAMPLE 2

The sensitivity to CO gas and ethanol of a gas detecting device using In instead of Sn as used in Example 1 was measured. The result is that the sensitivity to 1000 ppm CO gas was 900. In the case where a gas-sensitive substance did not thoroughly cover an insulating substrate, the substance showed a stable gas sensitivity for a long period as in Example 1.

EXAMPLE 3

In this Example 3, 800 parts by weight of Au was deposited prior to the deposition of 100 parts by weight of Sn, to mix Au with $SnO_2$ produced from the Sn oxidation. The result is that the sensitivity to 1000 ppm CO gas was 2400. When the deposited amount of Au exceeded 900 parts by weight per 100 parts by weight of Sn, the $SnO_2$ could not maintain its semiconductivity, resulting in substantial gas insensitivity of the device. An electrode may contain Au at a ratio of 900 parts or more by weight per 100 parts by weight of Sn, so that Au can function as an electrode.

In the case where the gas-sensitive substance partly did not cover the insulating substrate, the gas sensitivity was stable for a long period as in Example 1.

As is clearly indicated by these results, the CO-gas detecting device according to the present invention is obtained by forming a film containing as the principal ingredient at least one of Sn or In, depositing Pt as a catalytic layer on the surface of a gas-sensitive film layer obtained by oxidizing the principal ingredient, and mixing Au with $SnO_2$ to improve the CO-gas sensitivity of the device. The CO-gas detecting device shows a high gas sensitivity due to its simple structure without using a carrier such as $Al_2O_3$, and it has a stable gas sensitivity stable for a long period. The present device has extremely great industrial value.

What is claimed is:

1. A thin film gas-sensitive device comprising:
   an insulating substrate having a pair of electrodes disposed theron;
   a gas-sensitive layer, having a gas sensitive substance, deposited on the insulating substrate and electrodes; and
   a catalytic layer deposited on the gas-sensitive layer and insulating substrate as a non-continuous layer;
   wherein the insulating substrate is partly uncovered because the electrodes, the gas-sensitive layer containing the gas-sensitive substance and the catalytic layer do not thoroughly cover the substrate.

2. A gas-sensitive device according to claim 1, wherein the gas-sensitive substance comprises at least one of $SnO_2$ or $In_2O_3$.

3. A gas-sensitive device according to claim 1 for use in detecting CO-gas, wherein the device contains less than 900 parts by weight of Au per 100 parts by weight of Sn in the gas-sensitive layer.

4. A gas-sensitive device according to claim 1, wherein the catalytic layer is of an average thickness of 5 nm or less and comprises at least one of Pt and Pd.

5. A gas-sensitive device according to claim 3, wherein the gas sensitive layer contains Sn in the form of $SnO_2$.

6. A gas sensitive device according to claim 1, wherein the electrodes are comb-shaped.

7. A gas-sensitive device comprising:
   an insulating substrate;
   a pair of electrodes disposed on the substrate;
   a gas-sensitive substance deposited on portions of the substrate and the electrodes such that the substrate and the electrodes are only partially covered by the gas-sensitive substance; and
   a catalyst deposited on portions of the gas-sensitive substance and the substrate such that the gas-sensitive substance and the substrate are only partially covered by the catalyst.

8. The gas-sensitive device of claim 7, wherein the gas-sensitive substance comprises at least one of $SnO_2$ or $In_2O_3$.

9. The gas-sensitive device of claim 7, wherein the gas-sensitive substance comprises a mixture of Au and $SnO_2$, the mixture being less than 900 parts by weight of Au per 100 parts by weight of Sn.

10. The gas-sensitive device of claim 7, wherein the catalyst is one of Pt and Pd.

11. The gas-sensitive device of claim 10, wherein the catalyst is deposited as a non-continuous layer having an average thickness of no more than 5 nm.

12. A method of producing the gas-sensitive device according to claim 7, comprising:
   providing the insulating substrate;
   forming the pair of electrodes on the substrate;
   depositing a selected average thickness of the gas-sensitive substance in a vacuum on the electrodes and substrate;
   thermally treating the gas-sensitive substance to oxidize the gas-sensitive substance; and
   depositing a selected average thickness of the catalyst on the substrate and gas-sensitive substance.

13. The method according to claim 12, wherein the average thickness of the gas-sensitive substance is 13 nm.

14. The method according to claim 12, wherein the average thickness of the catalyst is 5 nm.

15. The method according to claim 12, wherein during depositing of the gas-sensitive substance and the catalyst, the selected average thicknesses are measured using a crystal oscillator.

16. The method according to claim 12, wherein depositing a selected average thickness of the gas-sensitive substance in a vacuum on the electrodes and substrate comprises:
   depositing less than 900 parts by weight of Au; and
   depositing 100 parts by weight of Sn,
and wherein during the step of thermally treating the gas-sensitive substance to oxidize the gas-sensitive substance, $SnO_2$ is formed and the Au mixes with the $SnO_2$.

* * * * *